United States Patent [19]

Quadranti et al.

[11] Patent Number: 4,840,663

[45] Date of Patent: Jun. 20, 1989

[54] SYNERGISTIC COMPOSITION AND METHOD FOR SELECTIVE WEED CONTROL IN RICE

[75] Inventors: Marco Quadranti, Brugg; Wilheim Schmidli, Münchwilen; Andreas Zoschke, Basel, all of Switzerland

[73] Assignee: Ciba-Geigy Corporation, Ardsley, N.Y.

[21] Appl. No.: 107,202

[22] Filed: Oct. 13, 1987

[30] Foreign Application Priority Data

Oct. 22, 1986 [CH] Switzerland .................. 4216/86

[51] Int. Cl.⁴ .................................. A01N 43/66
[52] U.S. Cl. ........................................ 71/93; 71/90; 71/91; 71/92; 71/100; 71/116; 71/118; 71/124; 71/88; 71/108; 71/117; 71/94; 71/121; 71/87
[58] Field of Search .................................. 71/118, 93

[56] References Cited

U.S. PATENT DOCUMENTS 4,168,965 9/1979 Vogel et al. .................. 71/118
4,479,821 10/1984 Meyer et al. .................. 71/93

FOREIGN PATENT DOCUMENTS 0044807 1/1982 European Pat. Off. .
0051466 6/1982 European Pat. Off. .
0087780 5/1984 European Pat. Off. .
2247076 4/1974 Fed. Rep. of Germany .
2822155 11/1979 Fed. Rep. of Germany .
3108873 9/1982 Fed. Rep. of Germany .
3419050 11/1985 Fed. Rep. of Germany .

OTHER PUBLICATIONS

Pesticide Manual, 5th Ed.
C.A., vol. 86, 51581y (1977).

Primary Examiner—Glennon H. Hollrah
Assistant Examiner—A. A. Owens
Attorney, Agent, or Firm—Kevin T. Mansfield; Edward McC. Roberts

[57] ABSTRACT

Compositions that contain, in admixture with one another, as active ingredient, on the one hand N-[2-(2-methoxyethoxy)-phenylsulphonyl]-N'-(4,6-dimethoxy-1,3,5-triazin-2-yl)-urea of the formula

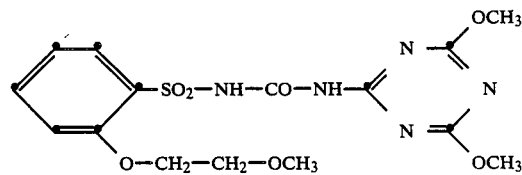

and on the other hand one or two of the active ingredients of the formulae II, III, IV, V, VI, VII, VIII, IX, X, XI, XII, XIII, XIV and XV defined herein exhibit synergistic herbicidal action in rice.

8 Claims, No Drawings

SYNERGISTIC COMPOSITION AND METHOD FOR SELECTIVE WEED CONTROL IN RICE

The present invention relates to a synergistic composition that contains a herbicidal active ingredient combination that is extremely suitable for selective weed control in rice crops. The invention relates also to a method for controlling weeds in rice and to the use of the novel composition.

The most common and important weeds in rice at present are species of the genera Alisma (water plantain); Ammania; Cyperus (cypress grass); Echinochloa (barnyard grass); Eleocharis (spike rush); Fimbristylis (fringe rush); Scirpus (bulrush) and Monochoria.

N-[2-(2-methoxyethoxy)-phenylsulphonyl]-N'-(4,6-dimethoxy-1,3,5-triazin-2-yl)-urea of the formula I (I)

has proved to be an excellent selective herbicide against weeds in crops of useful plants. That active ingredient is described, together with its manufacture and use, in U.S. Pat. No. 4 479 821.

In addition, compounds of the formulae II, III, IV, V, VI, VII, VIII, IX, X, XI, XII, XIII, XIV and XV are also known as selective herbicides. Some of them are already commercially available.

The formula II (II)

in which $R^1$ represents $C_1$–$C_4$-alkoxycarbonyl or $C_1$–$C_4$-alkoxy, covers the following embodiments:

IIa: 5-(2,4-dichlorophenoxy)-2-nitrobenzoic acid methyl ester, known from Pesticide Manual 5th Ed. (1977), 41, The British Crop Protection Council, London; and IIb: 4-(2,4-dichlorophenoxy)-2-methoxynitrobenzene, known from Pesticide Manual 5th Ed. (1977), 175, The British Crop Protection Council, London;

The formula III (III)

in which $R^2$ represents chlorine or methyl, covers the following individual active ingredients:

IIIa: 2,4-dichlorophenoxyacetic acid, known from Pesticide Manual 5th Ed. (1977), 330, The British Crop Protection Council, London; and IIIb: 4-chloro-2-methylphenoxyacetic acid, known from Pesticide Manual 5th Ed. (1977), 330, The British Crop Protection Council, London.

The formula IV (IV)

in which $R^3$ represents ethyl or 1,2-dimethylpropyl, covers the following embodiments:

IVa: 2,4-bis-ethylamino-6-methylthio-1,3,5-triazine, known from Pesticide Manual 5th Ed. (1977), 472, The British Crop Protection Council, London; and IVb: 2-[(1,2-dimethylpropyl)amino]-4-ethylamino-6-methylthio-1,3,5-triazine, known from Pesticide Manual 5th Ed. (1977), 197, The British Crop Protection Council, London.

The formula V (V)

in which $R^4$ represents $C_1$–$C_4$-alkoxy or $C_1$–$C_4$-alkoxymethyl, covers the following embodiments:

Va: N-(butoxymethyl)-2-chloro-N-(2,6-diethylphenyl)acetamide, known from Pesticide Manual 5th Ed. (1977), 60, The British Crop Protection Council, London; and Vb: N-(propoxyethyl)-2-chloro-N-(2,6-diethylphenyl)acetamide, known from Pesticide Manual 7th Ed. (1983), 9970, The British Crop Protection Council, London.

The formula VI (VI)

in which $R^5$ represents 2-(2-chloroethoxy)-phenyl, 2-methoxycarbonylbenzyl or 4-ethoxycarbonyl-1-methyl-5-pyrazolyl, $R^6$ represents methoxy or methyl and A represents nitrogen or the methine group, covers especially the following individual substances:

VIa: N-[2-(2-chloroethoxy)-phenylsulphonyl]-N'-(4-methoxy-6-methyl-1,3,5-triazin-2-yl)-urea, known from European Patent EP-A-44807;

VIb: N-(2-methoxycarbonylbenzylsulphonyl)-N'-(4,6-dimethoxypyrimidin-2-yl)-urea, known from EP-A-51466; and VIc: N-(4-ethoxycarbonyl-1-methylpyrazol-5-ylsulphonyl)-N'-(4,6-dimethoxypyrimidin-2-yl)-urea, known from EP-A-87780.

The formula VII

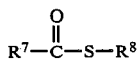

(VII)

in which R⁷ represents 1-piperidinyl, 1-hexahydroazepinyl or diethylamino and R⁸ represents ethyl, 4-chlorobenzyl or 1,1-dimethylbenzyl, covers especially the following specific embodiments:

VIIa: S-ethyl-N,N-hexamethylene thiocarbamate, known from Pesticide Manual 5th Ed. (1977), 369, The British Crop Protection Council, London;

VIIb: S-1,1-dimethylbenzyl-N,N-pentamethylene thiocarbamate, known from JP-PS 51 098 331; and VIIc: S-4-chlorobenzyl-N,N-diethyl thiocarbamate, known from Pesticide Manual 5th Ed. (1977), 106, The British Crop Protection Council, London.

The compounds of the formulae VIII, IX, X, XI, XII, XIII, XIV and XV are represented by the following formulae:

3,7-dichloroquinoline-8-carboxylic acid of the formula VIII

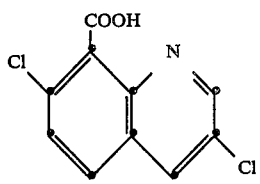

known from DE-OS No. 3 108 873;
2-(2-naphthyloxy)-propionic acid methyl ester of the formula IX

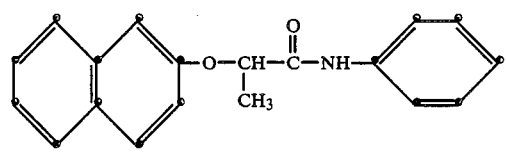

known from DE-OS No. 2 247 076;
N-(1-ethylpropyl)-3,4-dimethyl-2,6-dinitroaniline of the formula X

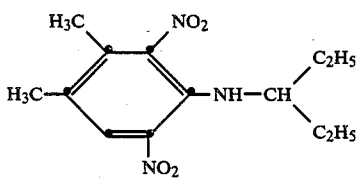

known from Pesticide Manual 7th Ed. (1983) 9390, The British Crop Protection Council, London;
5-tert.-butyl-3-(2,4-dichloro-5-isopropoxyphenyl)-1,3,4-oxadiazol-2-one of the formula XI

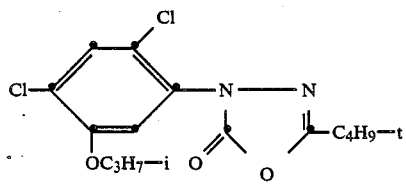

known from Pesticide Manual 5th Ed. (1977), 393, The British Crop Protection Council, London;
3-isopropyl-1H-benzo-2,1,3-thiadiazin-4-one-2,2-dioxide of the formula XII

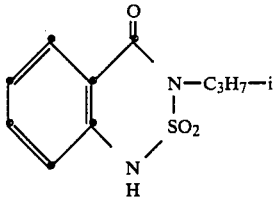

known from Pesticide Manual 5th Ed. (1977), 35, The British Crop Protection Council, London;
2-(2-benzothiazolyloxy)-N-methylacetanilide of the formula XIII

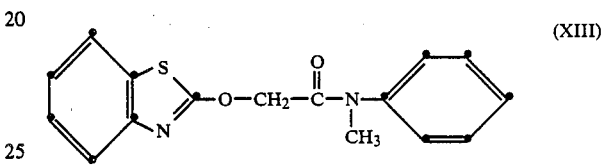

known from DE-OS No. 2 822 155;
3,4-dichloropropionanilide of the formula XIV

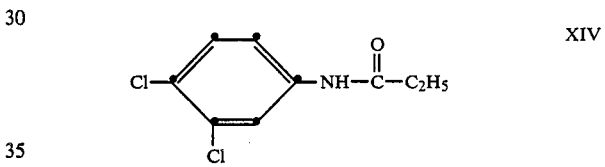

known from Pesticide Manual 5th Ed. (1977), 439, The British Crop Protection Council, London; and
S-2-methylpiperidinocarbonylmethyl-O,O-dipropyl-dithiophosphoric acid ester of the formula XV

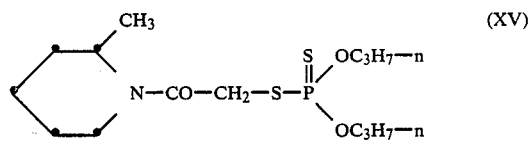

known from Pesticide Manual 5th Ed. (1977), 427, The British Crop Protection Council, London.

It has surprisingly been found that a quantitatively variable combination of two active ingredients, on the one hand active ingredient I and on the other hand an active ingredient selected from the classes II, III, IV, V, VI, VII, VIII, IX, X, XI, XII, XIII, XIV and XV, produces a synergistic effect that is capable of controlling the majority of all important rice weeds without damaging the rice crop. The principal weeds in rice crops, such as a species of the genera Alisma, Ammania, Cyperus, Echinochloa, Eleocharis, Fimbristylis, Scirpus and Monochoria, are destroyed selectively both in the preemergence and the postemergence method.

There is therefore proposed according to the present invention a novel synergistic composition for the selective control of weeds that contains, in admixture with one another, as active ingredient, on the one hand N-[2-(2-methoxyethoxy)-phenylsulphonyl]-N'(4,6-dimethoxy-1,3,5-triazin-2-yl)-urea of the formula I

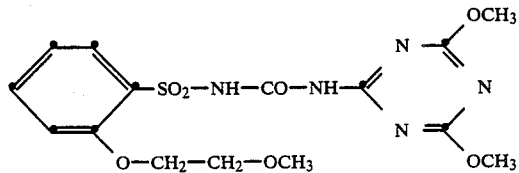

and on the other hand an active ingredient of the formula II

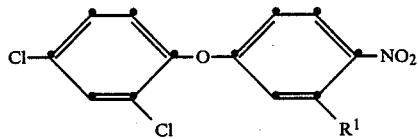

in which $R^1$ represents $C_1$–$C_4$-alkoxycarbonyl or $C_1$–$C_4$-alkoxy, or an active ingredient of the formula III

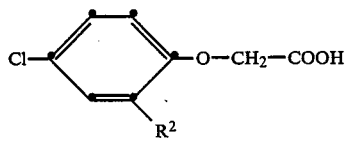

in which $R^2$ represents chlorine or methyl, or an active ingredient of the formula IV

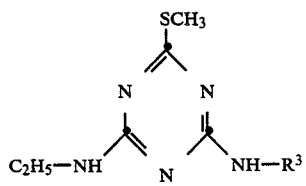

in which $R^3$ represents ethyl or 1,2-dimethylpropyl, or an active ingredient of the formula V

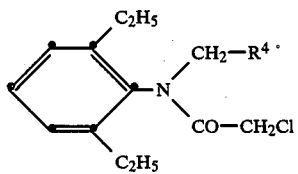

in which $R^4$ represents $C_1$–$C_4$-alkoxy or $C_1$–$C_4$-alkoxymethyl, or an active ingredient of the formula VI

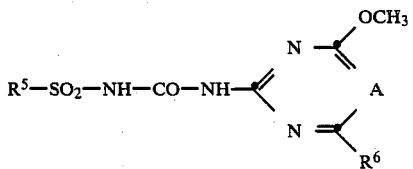

in which $R^5$ represents 2-(2-chloroethoxy)-phenyl, 2-methoxycarbonylbenzyl or 4-ethoxycarbonyl-1-methyl-5-pyrazolyl, $R^6$ represents methoxy or methyl and A represents nitrogen or the methine group, or an active ingredient of the formula VII

in which $R^7$ represents 1-piperidinyl, 1-hexahydroazepinyl or diethylamino and $R^8$ represents ethyl, 4-chlorobenzyl or 1,1-dimethylbenzyl, or the compound of the formula VIII

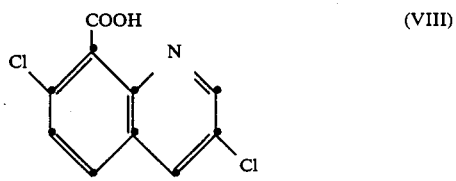

or the compound of the formula IX

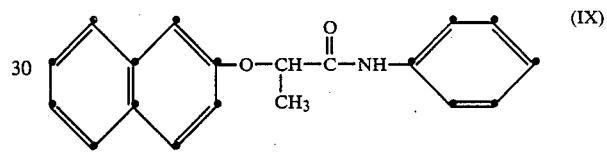

or the compound of the formula X

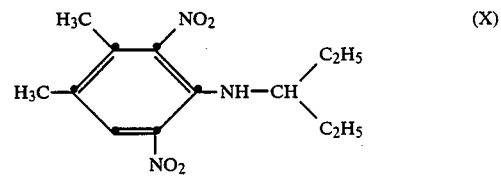

or the compound of the formula XI

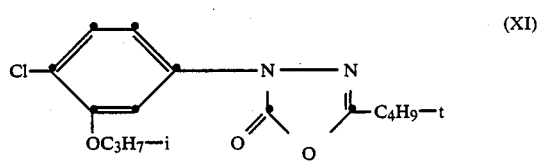

or the compound of the formula XII

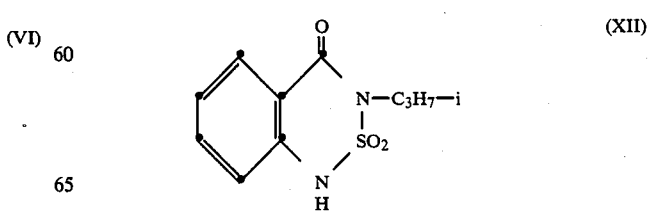

or the compound of the formula XIII

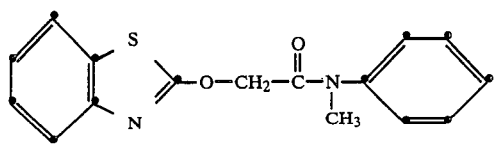

or the compound of the formula XIV

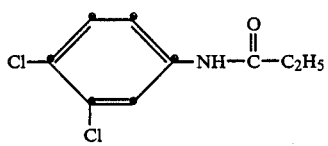

or the compound of the formula XV

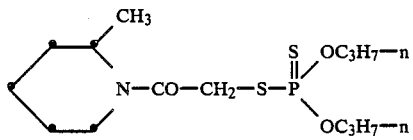

It is extremely surprising that a combination of the active ingredient of the formula I and an active ingredient of the formula II, III, IV, V, VI VII, VIII, IX, X, XI, XII, XIII, XIV or XV not only brings about an additive broadening of the spectrum of action to cover weeds that are normally associated with rice, which would be expected in principle, but also achieves a synergistic effect that broadens the range of action of both preparations in two respects.

Firstly, the rates of application of the individual compounds I and II, III, IV, V, VI, VII, VIII, IX, X, XI, XII, XIII, XIV or XV are markedly reduced while the high level of action is maintained unchanged and, secondly, the combined mixture still achieves a high degree of weed control even where the two compounds individually are entirely without effect when the rates of application are too low. The result of this is a considerable broadening of the weed spectrum and an additional increase in the safety margin in rice, as is necessary and desirable in case of inadvertent overdosage of the active ingredient.

The composition according to the invention can be used both in rice crops grown in water (paddy rice) and in rice crops grown on dry ground (upland rice).

The active ingredient combination according to the invention contains an active ingredient of the formula I and an active ingredient of the formula II, III, IV, V, VI, VII, VIII, IX, X, XI, XII, XIII, XIV or XV in any mixture ratio, generally with an excess of the one component over the other. The mixture ratio is of so little importance that both excesses of the component of the formula I and excesses of the component of the formula II, III, IV, V, VI, VII, VIII, IX, X, XI, XII, XIII, XIV or XV are tolerated. Preferred mixture ratios of active ingredient I to the co-component of the formula II, III, IV, V, VI, VII, VIII, IX, X, XI, XII, XIII, XIV or XV are from 1:1 to 1:2000, especially from 1:5 to 1:500. The active ingredient combinations according to the invention exhibit outstanding action against weeds while having no appreciable effect on the rice crops at the advantageously used rates of application of from 0.005 to 3 kg, preferably from 0.01 to 1 kg, per hectare.

Combinations of compound I with the following individual active ingredients have proved to be outstandingly effective synergistic active ingredient mixtures:

(a) N-(butoxymethyl)-2-chloro-N-(2,6-diethylphenyl)acetamide [compound Va];

(b) N-(propoxyethyl)-2-chloro-N-(2,6-diethylphenyl)acetamide [compound Vb];

(c) S-4-chlorobenzyl-N,N-diethylthiocarbamate [compound VIIc];

(d) 3,7-dichloroquinoline-8-carboxylic acid [compound VIII];

(e) 2-(2-benzothiazolyloxy)-N-methylacetanilide [compound XIII]; and (f) S-2-methylpiperidinocarbonylmethyl-O,O-dipropyldithiophosphoric acid ester [compound XV].

Of the above, especially preferred synergistic combination partners of the compound of the formula I are the active ingredients of Vb, VIIc, VIII and XIII.

The formulations, i.e. the compositions or preparations containing the active ingredient mixture according to the invention and, where appropriate, a solid or liquid adjuvant, are manufactured in known manner, for example by intimately mixing and/or grinding the active ingredients with extenders, such as, for example, solvents, solid carriers and, where appropriate, surface-active compounds (surfactants).

Suitable solvents are: aromatic hydrocarbons, preferably the fractions $C_8$ to $C_{12}$, such as, for example, xylene mixtures or substituted naphthalenes, phthalic acid esters, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, and also optionally epoxidised vegetable oils, such as epoxidised coconut oil or soybean oil, or water.

The solid carriers used, for example for dusts and dispersible powders, are generally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, such as, for example, pumice, broken brick, sepiolite or bentonite, and suitable nonsorbent carriers are, for example, calcite or sand. In addition, it is possible to use a large number of pre-granulated materials of inorganic or organic nature, such as, especially, dolomite or pulverised plant residues, such as, for example, cork powder or sawdust.

Especially advantageous, application-facilitating adjuvants that can result in a great reduction in the rates of application are also natural (animal or vegetable) or synthetic phospholipids from the series of cephalins and lecithins, such as, for example, phosphatidylethanolamine, phosphatidylserine, phosphatidylcholine, sphingomyelin, phosphatidylinositol, phosphatidylglycerol, lysolecithin, plasmalogen or cardiolipin, which can be obtained, for example, from animal or vegetable cells, especially from the brain, heart, lung, liver, egg yolks or soybeans. Commercial mixtures that can be used are, for example, phosphatidylcholine mixtures. Synthetic phospholipids are, for example, dioctanoylphosphatidylcholine and dipalmitoylphosphatidylcholine.

Suitable surface-active compounds are nonionic, cationic and/or anionic surfactants having good emulsifying, dispersing and wetting properties. The term "surfactants" should also be understood as meaning mixtures of surfactants.

Suitable anionic surfactants may be both so-called water-soluble soaps and water-soluble synthetic surfaceactive compounds.

There may be mentioned as soaps the alkali metal salts, alkaline earth metal salts and unsubstituted or substituted ammonium salts of higher fatty acids ($C_{10}$–$C_{22}$), such as, for example, the sodium or potassium salts of oleic or stearic acid, or of natural fatty acid mixtures, which can be obtained, for example, from coconut or tallow oil. Fatty acid methyltaurine salts should also be mentioned.

So-called synthetic surfactants are, however, more often used, especially fatty sulphonates, fatty sulphates, sulphonated benzimidazole derivatives or alkylarylsulphonates.

The fatty sulphonates or fatty sulphates are generally in the form of alkali metal salts, alkaline earth metal salts or unsubstituted or substituted ammonium salts and have an alkyl radical having from 8 to 22 carbon atoms, alkyl also including the alkyl moiety of acyl radicals, for example the sodium or calcium salt of lignosulphonic acid, of dodecylsulphuric acid ester or of a fatty alcohol sulphate mixture produced from natural fatty acids. These also include the salts of sulphuric acid esters and sulphonic acids of fatty alcohol/ethylene oxide adducts. The sulphonated benzimidazole derivatives contain preferably 2 sulphonic acid groups and one fatty acid radical having from 8 to 22 carbon atoms. Alkylarylsulphonates are, for example, the sodium, calcium or triethanolamine salts of dodecylbenzenesulphonic acid, of dibutylnaphthalenesulphonic acid or of a naphthalenesulphonic acid/formaldehyde condensation product.

Also suitable are corresponding phosphates, such as, for example, salts of the phosphoric acid ester of an adduct of p-nonylphenol with from 4 to 14 moles of ethylene oxide.

Suitable nonionic surfactants are especially polyglycol ether derivatives of aliphatic or cycloaliphatic alcohols, of saturated or unsaturated fatty acids and of alkylphenols, that may contain from 3 to 30 glycol ether groups and from 8 to 20 carbon atoms in the (aliphatic) hydrocarbon radical and from 6 to 18 carbon atoms in the alkyl radical of the alkylphenols.

Further suitable nonionic surfactants are the water-soluble adducts of polyethylene oxide with polypropylene glycol, ethylenediaminopolypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The said compounds normally contain from 1 to 5 ethylene glycol units per propylene glycol unit.

There may be mentioned as examples of nonionic surfactants nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Also suitable are fatty acid esters of polyoxyethylenesorbitan, such as polyoxyethylenesorbitan trioleate.

Cationic surfactants are especially quaternary ammonium salts that contain, as N-substituent, at least one alkyl radical having from 8 to 22 carbon atoms and, as further substituents, lower unsubstituted or halogenated alkyl, benzyl or lower hydroxyalkyl radicals. The salts are preferably in the form of halides, methyl sulphates or ethyl sulphates, for example stearyltrimethylammonium chloride or benzyldi(2-chloroethyl)ethylammonium bromide.

The surfactants customarily employed in the art of formulation are described, inter alia, in the following publications:

"McCutcheon's Detergents and Emulsifiers Annual" MC Publishing Corp., Ridgewood, N.J., 1981;

H. Stache, "Tensid-Taschenbuch", 2nd Edition, C. Hanser Verlag, Munich, Vienna, 1981;

M. and J. Ash "Encyclopedia of Surfactants", vols. I–III, Chemical Publishing Co., New York, 1980–1981.

The agrochemical preparations generally contain from 0.1 to 95%, especially from 0.1 to 80%, active ingredient mixture of the formulae I and II, III, IV, V, VI, VII, VIII, IX, X, XI, XII, XIII, XIV or XV, from 1 to 99.9% solid or liquid adjuvant and from 0 to 25%, especially from 0.1 to 25%, surfactant.

Preferred formulations are composed especially of the following constituents (% = percentage by weight):

| Emulsifiable concentrates | | | |
|---|---|---|---|
| active ingredient mixture | 1–20%, | preferably | 5–10% |
| surface-active agent | 5–30%, | preferably | 10–20% |
| liquid carrier | 50–94%, | preferably | 70–85% |
| Dusts | | | |
| active ingredient mixture | 0.1–10%, | preferably | 0.1–1% |
| solid carrier | 99.9–90%, | preferably | 99.9–99% |
| Suspension concentrates | | | |
| active ingredient mixture | 5–75%, | preferably | 10–50% |
| water | 94–25%, | preferably | 88–30% |
| surface-active agent | 1–40%, | preferably | 2–30% |
| Wettable powders | | | |
| active ingredient mixture | 0.5–90%, | preferably | 1–80% |
| surface-active agent | 0.5–20%, | preferably | 1–15% |
| solid carrier | 5.0–95%, | preferably | 15–90% |
| Granulates | | | |
| active ingredient mixture | 0.5–30%, | preferably | 3–15% |
| solid carrier | 99.5–70%, | preferably | 97–85% |

Whereas commercial products will preferably be formulated as concentrates, the end user will normally employ dilute formulations. The forms of application can be diluted to concentrations as low as 0.001% active ingredient.

Other biocidal active ingredients or compositions can be mixed with the described compositions according to the invention. For example, the novel compositions may contain, in addition to the mentioned compounds of the general formula I and of the formula II, III, IV, V, VI, VII, VIII, IX, X, XI, XII, XIII, XIV or XV, insecticides, fungicides, bactericides, fungistatics, bacteriostatics and nematocides in order to broaden the spectrum of action. It is also possible to add antagonists (safeners) in order to protect the cultivated plants from inadvertent overdoses of herbicides or herbicide mixtures.

The compositions according to the invention are generally formulated, in detail, in accordance with the following Examples:

FORMULATION EXAMPLES

Example F1

Formulation Examples for synergistic active ingredient mixtures of the formulae I and II, III, IV, V, VI, VII, VIII, IX, X, XI, XII, XIII, XIV or XV (%=percentage by weight)

| (a) Wettable powders | (a) | (b) | (c) | (d) |
|---|---|---|---|---|
| active ingredient I | 10% | 20% | 5% | 30% |
| one of the active ingredients II, III, IV, V, VI, VII, VIII, IX, X, XI, XII, XIII, XIV and XV | 10% | 40% | 15% | 30% |
| Na lignosulphonate | 5% | 5% | 5% | 5% |
| Na lauryl sulphate | 3% | — | 3% | — |
| Na diisobutylnaphthalene sulphonate | — | 6% | — | 6% |
| octylphenol polyethylene glycol ether (7–8 mol EO) | — | 2% | — | 2% |
| highly dispersed silicic acid | 5% | 27% | 5% | 27% |
| kaolin | 67% | — | 67% | — |

The active ingredient mixture is mixed well with the adjuvants and ground well in a suitable mill. Wettable powders are obtained that can be diluted with water to form suspensions of any desired concentration.

| (b) Emulsion concentrate | (a) | (b) | (c) |
|---|---|---|---|
| active ingredient I | 5% | 5% | 12% |
| one of the active ingredients II, III, IV, V, ,I, VII, VIII, IX, X, XI, XII, XIII, XIV and XV | 5% | 20% | 13% |
| octylphenol polyethylene glycol ether (4–5 mol EO) | 3% | 3% | 3% |
| Ca dodecylbenzenesulphonate | 3% | 3% | 2% |
| castor oil polyglycol ether (36 mol EO) | 4% | 4% | 4% |
| cyclohexanone | 30% | 30% | 31% |
| xylene mixture | 50% | 35% | 35% |

Emulsions of any desired concentration can be produced from these concentrates by dilution with water.

| (c) Dusts | (a) | (b) | (c) | (d) |
|---|---|---|---|---|
| active ingredient I | 2% | 4% | 2% | 4% |
| one of the active ingredients II, III, IV, V, VI, VII, VIII, IX, X, XI, XII, XIII, XIV and XV | 3% | 4% | 4% | 8% |
| talcum | 95% | — | 94% | — |
| kaolin | — | 92% | — | 88% |

Ready-for-use dusts are obtained by mixing the active ingredient mixture with the carrier and grinding the mixture in a suitable mill.

| (d) Extruder granulate | (a) | (b) | (c) |
|---|---|---|---|
| active ingredient I | 5% | 3% | 5% |
| one of the active ingredients II, III, IV, V, VI, VII, VIII, IX, X, XI, XII, XIII, XIV and XV | 5% | 7% | 15% |
| Na lignosulphonate | 2% | 2% | 2% |
| carboxymethylcellulose | 1% | 1% | 1% |
| kaolin | 87% | 87% | 77% |

The active ingredient mixture is mixed and ground with the adjuvants, and moistened with water. The mixture is extruded and then dried in a stream of air.

| (e) Coated granulate | (a) | (b) |
|---|---|---|
| active ingredient I | 1.5% | 3% |
| one of the active ingredients II, III, IV, V, VI, VII, VIII, IX, X, XI, XII, XIII, XIV and XV | 1.5% | 5% |
| polyethylene glycol (MW 200) | 3% | 3% |
| kaolin | 94% | 89% |

The finely ground active ingredient mixture is applied uniformly, in a mixer, to the kaolin, which has been moistened with polyethylene glycol. Dust-free coated granulates are thus obtained.

| (f) Suspension concentrate | (a) | (b) |
|---|---|---|
| active ingredient I | 20% | 20% |
| one of the active ingredients II, III, IV, V, VI, VII, VIII, IX, X, XI, XII, XIII, XIV and XV | 20% | 40% |
| ethylene glycol | 10% | 10% |
| nonylphenol polyethylene glycol ether (15 mol EO) | 6% | 6% |
| Na lignosulphonate | 10% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 12% |

The finely ground active ingredient mixture is intimately mixed with the adjuvants. A suspension concentrate is thus obtained from which suspensions of any desired concentration can be produced by dilution with water.

A synergistic effect is always present in the case of herbicides when the herbicidal action of the active ingredient combination of I and II, III, IV, V, VI, VII, VIII, IX, X, XI, XII, XIII, XIV or XV is greater than the total action of the active ingredients applied individually.

The expected herbicidal action E for a given combination of two herbicides can be calculated as follows (cf. COLBY, S. R., "Calculating synergistic and antagonistic response of herbicide combinations", Weeds 15, pages 20–22, 1967);

$$E = X + \frac{Y \cdot (100 - X)}{100}$$

in which:
- X = percentage inhibition of growth in the case of treatment with a herbicide I at a rate of application of p kg per hectare in comparison with the untreated control (=0%)
- Y = percentage inhibition of growth in the case of treatment with a herbicide II, III, IV, V, VI, VII, VIII, IX, X, XI, XII, XIII, XIV or XV at a rate of application of q kg per hectare in comparison with the untreated control.
- E = expected herbicidal action (percentage inhibition of growth in comparison with the untreated control) after treatment with herbicide mixture I and II, III, IV, V, VI, VII, VIII, IX, X, XI, XII, XIII, XIV or XV at a rate of application of p+q kg active ingredient per hectare.

If the action actually observed is greater than the expected value E, then synergism has been achieved.

The synergistic effect ascertained in the case of the above components according to the invention in mixtures of two active ingredients is also observed in mixtures of three active ingredient components. Such three-component mixtures form a further aspect of the present invention.

The synergistic three-component compositions according to the invention for selective weed control are characterised in that they contain, in admixture with one another, as active ingredient, on the one hand N-[2-(2-methoxyethoxy)-phenylsulphonyl]-N'-(4,6-dimethoxy-1,3,5-triazin-2-yl)-urea of the formula I

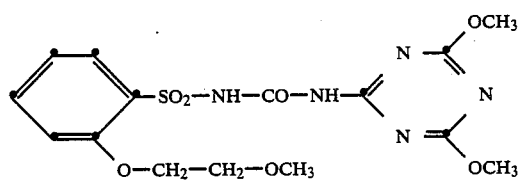

and on the other hand two active ingredients selected from the series consisting of the compounds of the formula II

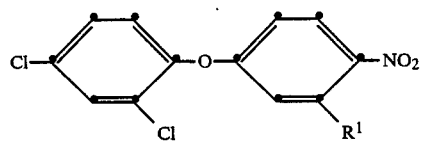

in which $R^1$ represents $C_1$-$C_4$-alkoxycarbonyl or $C_1$-$C_4$-alkoxy, the compounds of the formula III

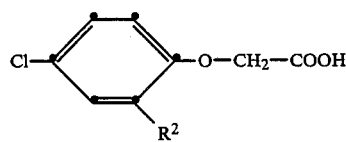

in which $R^2$ represents chlorine or methyl,
the compounds of the formula IV

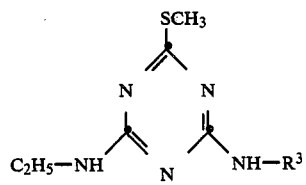

in which $R^3$ represents ethyl or 1,2-dimethylpropyl,
the compounds of the formula V

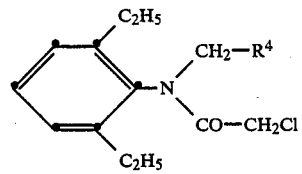

in which $R^4$ represents $C_1$-$C_4$-alkoxy or $C_1$-$C_4$-alkoxymethyl,
the compounds of the formula VI

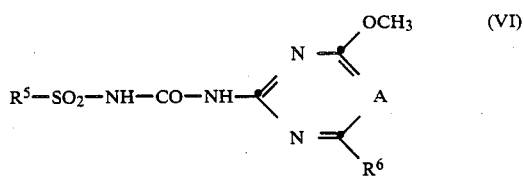

in which $R^5$ represents 2-(2-chloroethoxy)-phenyl, 2-methoxycarbonylbenzyl or 4-ethoxycarbonyl-1-methyl-5-pyrazolyl, $R^6$ represents methoxy or methyl and A represents nitrogen or the methine group,
the compounds of the formula VII

in which $R^7$ represents 1-piperidinyl, 1-hexahydroazepinyl or diethylamino and $R^8$ represents ethyl, 4-chlorobenzyl or 1,1-dimethylbenzyl,
the compound of the formula VIII

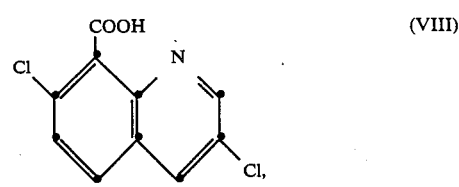

the compound of the formula IX

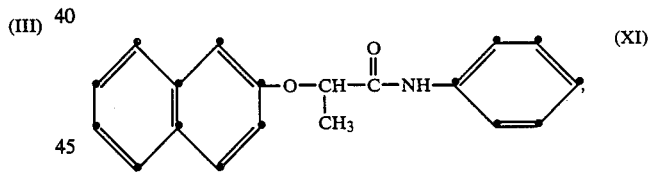

the compound of the formula X

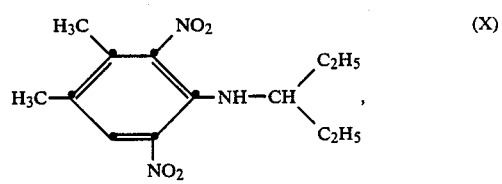

the compound of the formula XI

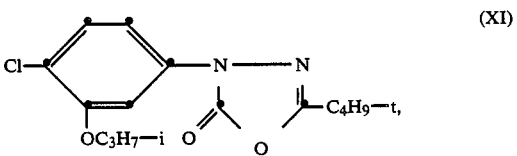

the compound of the formula XII

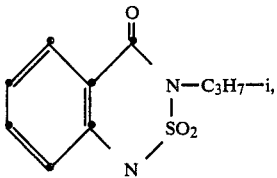

the compound of the formula XIII

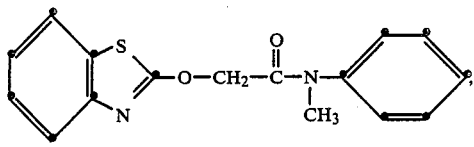

the compound of the formula XIV

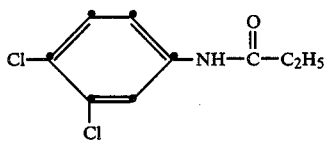

and the compound of the formula XV

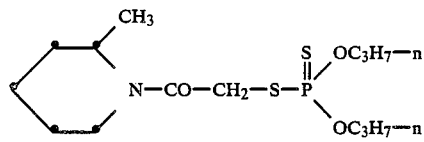

It is extremely surprising that a combination of the active ingredient of the formula I and two active ingredients of the formulae II, III, IV, V, VI, VII, VIII, IX, X, XI, XII, XIII, XIV and XV not only brings about an additive broadening of the spectrum of action to cover weeds that are normally associated with rice, which would be expected in principle, but also achieves a synergistic effect.

The expected herbicidal action of a three-component mixture can be calculated according to DE-OS No. 34 19 050 by means of the following formula:

$$E = X + Y + Z - \frac{(X \cdot Y + X \cdot Z + Y \cdot Z)}{100} + \frac{X \cdot Y \cdot Z}{10000}$$

In that formula the symbols E, X and Y have the meanings given above while Z has the same meaning as Y with the proviso that a different herbicide is selected from the series II, III, IV, V, VI, VII, VIII, IX, X, XI, XII, XIII, XIV and XV from that chosen in the case of Y.

If the action actually observed is greater than the expected value E, then synergism has also been achieved in the case of a three-component mixture.

The three-component active ingredient mixtures according to the invention can be formulated in accordance with the same principles as can the two-component mixtures.

The mixture ratios of the three-component mixtures are to a great extent unimportant. As a rule, the amount of component I is less than the amount of the other two components of the mixture. For example, the components of the mixture are generally in ratios of from 1:1:1 to 1:100:100. The first figure represents the compound of the formula I and the other two figures represent the two co-components from the series consisting of the compounds of the formulae II, III, IV, V, VI, VII, VIII, IX, X, XI, XII, XIII, XIV and XV. The mixture ratios are preferably from 1:5:5 to 1:20:20.

The preferred co-components for the compounds of the formula I are in the group 2,4-dichlorophenoxyacetic acid (compound IIIa)
N-(propoxyethyl)-2-chloro-N-(2,6-diethylphenyl)-acetamide (compound Vb),
S-ethyl-N,N-hexamethylene thiocarbamate (compound VIIa),
3,7-dichloroquinoline-8-carboxylic acid (compound VIII),
3,4-dichloropropionanilide (compound XIV), and
S-2-methylpiperidinocarbonylmethyl-O,O-dipropyldithiophosphoric acid ester (compound XV).

Preferred mixtures having three active ingredient components are compound I with compounds Vb and XV,
compound I with compounds VIII and XV,
compound I with compounds Vb and VIII,
compound I with compounds XIV and XV, and
compound I with compounds IIIa and XV.

The mixture that is especially preferred contains, together with active ingredient I, compounds Vb and VIII.

The rates of application of the three-component mixtures according to the invention are from 0.005 to 3 kg, preferably from 0.01 to 1 kg, per hectare.

The synergistic effect of the combinations of the active ingredients I and II, III, IV, V, VI, VII, VIII, IX, X, XI, XII, XIII, XIV or XV is demonstrated in the following Examples.

In order to simplify the structure of the tests and to obtain a better basis for comparison, in addition to the cultivated plant, rice, either *Monochoria vaginalis* or *Scirpus juncoides* was selected as a representative example of the weeds.

BIOLOGICAL EXAMPLES

Example B1

Greenhouse test 25-day-old rice plants of the type "Yamabiko" were planted in large containers in a greenhouse. Seeds of the rice weed Monochoria were sown between the rice plants. The containers were then watered and covered with a layer of water 2.5 cm deep. Three days after planting the rice and sowing the seeds a diluted concentrate of the active ingredients was added to the covering layer of water in amounts given in rate of application per hectare. The containers were kept covered with water at a temperature of 25° C. and at high air humidity until an evaluation was carried out 11 days later. The percentage inhibition of growth was recorded in comparison with the untreated control. The following linear scale was used as a standard:

100% = plants killed
50% = mean effect
0% = as untreated control

The results of the test are shown together with the expected values, calculated in accordance with the above-mentioned Colby formula, in the Tables in sections a, b, c, d and e. The Tables indicate the amounts of active ingredient applied in each case and the plants tested. Each of sections a, b, c, d and e contains three Tables. The first two Tables show the results obtained with the individual active ingredients and the third Table gives the expected values calculated according to Colby in comparison with the values ascertained experimentally.

(a) Activity of mixtures I with Va

Evaluation: 11 days after application in percentage inhibition of growth in comparison with the untreated control

| Compound I g a.i./ha | 16 | 8 | 4 | 2 | 1 |
|---|---|---|---|---|---|
| "Yamabiko" rice | 0 | 0 | 0 | 0 | 0 |
| Monochoria | 50 | 30 | 30 | 0 | 0 |

| Compound Va g a.i./ha | 60 | 30 | 15 | 8 | 4 |
|---|---|---|---|---|---|
| "Yamabiko" rice | 0 | 0 | 0 | 0 | 0 |
| Monochoria | 40 | 20 | 0 | 0 | 0 |

| rates of application in g a.i./ha | | "Yamabiko" rice | | Monochoria | |
|---|---|---|---|---|---|
| comp. I | comp. Va | effect found | expected value | effect found | expected value |
| 16 | 60 | 0 | 0 | 80 | 70 |
| 8 | 60 | 0 | 0 | 75 | 58 |
| 4 | 60 | 0 | 0 | 75 | 58 |
| 2 | 60 | 0 | 0 | 50 | 40 |
| 1 | 60 | 0 | 0 | 40 | 40 |
| 16 | 30 | 0 | 0 | 85 | 60 |
| 8 | 30 | 0 | 0 | 75 | 44 |
| 4 | 30 | 0 | 0 | 55 | 44 |
| 2 | 30 | 0 | 0 | 40 | 20 |
| 1 | 30 | 0 | 0 | 20 | 20 |
| 16 | 15 | 0 | 0 | 90 | 50 |
| 8 | 15 | 0 | 0 | 80 | 30 |
| 4 | 15 | 0 | 0 | 80 | 30 |
| 2 | 15 | 0 | 0 | 60 | 0 |
| 1 | 15 | 0 | 0 | 40 | 0 |
| 16 | 8 | 0 | 0 | 80 | 50 |
| 8 | 8 | 0 | 0 | 75 | 30 |
| 4 | 8 | 0 | 0 | 50 | 30 |
| 2 | 8 | 0 | 0 | 30 | 0 |
| 1 | 8 | 0 | 0 | 0 | 0 |
| 16 | 4 | 0 | 0 | 90 | 50 |
| 8 | 4 | 0 | 0 | 85 | 30 |
| 4 | 4 | 0 | 0 | 60 | 30 |
| 2 | 4 | 0 | 0 | 30 | 0 |
| 1 | 4 | 0 | 0 | 0 | 0 |

(b) Activity of mixtures I with Vb

Evaluation: 11 days after application in percentage inhibition of growth in comparison with the untreated control

| Compound I g a.i./ha | 16 | 8 | 4 | 2 | 1 |
|---|---|---|---|---|---|
| "Yamabiko" rice | 0 | 0 | 0 | 0 | 0 |
| Monochoria | 50 | 30 | 30 | 0 | 0 |

| Compound Vb g a.i./ha | 16 | 8 | 4 | | |
|---|---|---|---|---|---|
| "Yamabiko" rice | 0 | 0 | 0 | | |
| Monochoria | 30 | 20 | 0 | | |

| rates of application in g a.i./ha | | "Yamabiko" rice | | Monochoria | |
|---|---|---|---|---|---|
| comp. I | comp. Va | effect found | expected value | effect found | expected value |
| 16 | 16 | 0 | 0 | 90 | 65 |
| 8 | 16 | 0 | 0 | 80 | 51 |
| 4 | 16 | 0 | 0 | 90 | 51 |
| 2 | 16 | 0 | 0 | 80 | 30 |
| 1 | 16 | 0 | 0 | 20 | 30 |
| 16 | 8 | 0 | 0 | 80 | 60 |
| 8 | 8 | 0 | 0 | 70 | 44 |
| 4 | 8 | 0 | 0 | 70 | 40 |
| 2 | 8 | 0 | 0 | 50 | 20 |
| 1 | 8 | 0 | 0 | 20 | 20 |
| 16 | 4 | 0 | 0 | 70 | 30 |
| 8 | 4 | 0 | 0 | 60 | 30 |
| 4 | 4 | 0 | 0 | 60 | 30 |
| 2 | 4 | 0 | 0 | 30 | 0 |
| 1 | 4 | 0 | 0 | 10 | 0 |

(c) Activity of mixtures I with VIIc

Evaluation: 11 days after application in percentage inhibition of growth in comparison with the untreated control

| Compound I g a.i./ha | 16 | 8 | 4 | 2 | 1 |
|---|---|---|---|---|---|
| "Yamabiko" rice | 0 | 0 | 0 | 0 | 0 |
| Monochoria | 50 | 30 | 30 | 0 | 0 |

| Compound VIIc g a.i./ha | 250 | 125 | 60 | 30 | 15 |
|---|---|---|---|---|---|
| "Yamabiko" rice | 0 | 0 | 0 | 0 | 0 |
| Monochoria | 0 | 0 | 0 | 0 | 0 |

| rates of application in g a.i./ha | | "Yamabiko" rice | | Monochoria | |
|---|---|---|---|---|---|
| comp. I | comp. VIIc | effect found | expected value | effect found | expected value |
| 16 | 250 | 0 | 0 | 100 | 50 |
| 8 | 250 | 0 | 0 | 95 | 30 |
| 4 | 250 | 0 | 0 | 95 | 30 |
| 2 | 250 | 0 | 0 | 85 | 0 |
| 1 | 250 | 0 | 0 | 50 | 0 |
| 16 | 125 | 0 | 0 | 95 | 50 |
| 8 | 125 | 0 | 0 | 90 | 30 |
| 4 | 125 | 0 | 0 | 90 | 30 |
| 2 | 125 | 0 | 0 | 85 | 0 |
| 1 | 125 | 0 | 0 | 0 | 0 |
| 16 | 60 | 0 | 0 | 90 | 50 |
| 8 | 60 | 0 | 0 | 90 | 30 |
| 4 | 60 | 0 | 0 | 90 | 30 |
| 2 | 60 | 0 | 0 | 80 | 0 |
| 1 | 60 | 0 | 0 | 40 | 0 |
| 16 | 30 | 0 | 0 | 85 | 50 |
| 8 | 30 | 0 | 0 | 80 | 30 |
| 4 | 30 | 0 | 0 | 80 | 30 |
| 2 | 30 | 0 | 0 | 60 | 0 |
| 1 | 30 | 0 | 0 | 40 | 0 |
| 16 | 15 | 0 | 0 | 80 | 50 |
| 8 | 15 | 0 | 0 | 80 | 30 |
| 4 | 15 | 0 | 0 | 80 | 30 |
| 2 | 15 | 0 | 0 | 50 | 0 |
| 1 | 15 | 0 | 0 | 20 | 0 |

(d) Activity of mixtures I with XIII

Evaluation: 11 days after application in percentage inhibition of growth in comparison with the untreated control

| Compound I g a.i./ha | 16 | 8 | 4 | 2 | 1 |
|---|---|---|---|---|---|
| "Yamabiko" rice | 0 | 0 | 0 | 0 | 0 |
| Monochoria | 50 | 30 | 30 | 0 | 0 |

| Compound XIII g a.i./ha | 60 | 30 | 15 | 8 | 4 |
|---|---|---|---|---|---|
| "Yamabiko" rice | 0 | 0 | 0 | 0 | 0 |
| Monochoria | 10 | 0 | 0 | 0 | 0 | rates of applica-

-continued

| tion in g a.i./ha | | "Yamabiko" rice | | Monochoria | |
|---|---|---|---|---|---|
| comp. I | comp. XIII | effect found | expected value | effect found | expected value |
| 16 | 60 | 0 | 0 | 100 | 55 |
| 8 | 60 | 0 | 0 | 98 | 37 |
| 4 | 60 | 0 | 0 | 95 | 37 |
| 2 | 60 | 0 | 0 | 80 | 10 |
| 1 | 60 | 0 | 0 | 30 | 10 |
| 16 | 30 | 0 | 0 | 95 | 50 |
| 8 | 30 | 0 | 0 | 95 | 30 |
| 4 | 30 | 0 | 0 | 90 | 30 |
| 2 | 30 | 0 | 0 | 75 | 0 |
| 1 | 30 | 0 | 0 | 20 | 0 |
| 16 | 15 | 0 | 0 | 100 | 50 |
| 8 | 15 | 0 | 0 | 95 | 30 |
| 4 | 15 | 0 | 0 | 90 | 30 |
| 2 | 15 | 0 | 0 | 70 | 0 |
| 1 | 15 | 0 | 0 | 20 | 0 |
| 16 | 8 | 0 | 0 | 95 | 50 |
| 8 | 8 | 0 | 0 | 85 | 30 |
| 4 | 8 | 0 | 0 | 70 | 30 |
| 2 | 8 | 0 | 0 | 50 | 0 |
| 1 | 8 | 0 | 0 | 0 | 0 |
| 16 | 4 | 0 | 0 | 90 | 50 |
| 8 | 4 | 0 | 0 | 80 | 30 |
| 4 | 4 | 0 | 0 | 70 | 30 |
| 2 | 4 | 0 | 0 | 40 | 0 |
| 1 | 4 | 0 | 0 | 0 | 0 |

(e) Activity of mixtures I with XV

Evaluation: 11 days after application in percentage inhibition of growth in comparison with the untreated control

| Compound I g a.i./ha | 16 | 8 | 4 | 2 | 1 |
|---|---|---|---|---|---|
| "Yamabiko" rice | 0 | 0 | 0 | 0 | 0 |
| Monochoria | 50 | 30 | 30 | 0 | 0 |
| Compound XV g a.i./ha | 250 | 125 | 60 | 30 | 15 |
| "Yamabiko" rice | 0 | 0 | 0 | 0 | 0 |
| Monochoria | 10 | 0 | 0 | 0 | 0 |

| rates of application in g a.i./ha | | "Yamabiko" rice | | Monochoria | |
|---|---|---|---|---|---|
| comp. I | comp. XV | effect found | expected value | effect found | expected value |
| 16 | 250 | 0 | 0 | 95 | 55 |
| 8 | 250 | 0 | 0 | 90 | 37 |
| 4 | 250 | 0 | 0 | 90 | 37 |
| 2 | 250 | 0 | 0 | 85 | 10 |
| 1 | 250 | 0 | 0 | 70 | 10 |
| 16 | 125 | 0 | 0 | 95 | 50 |
| 8 | 125 | 0 | 0 | 95 | 30 |
| 4 | 125 | 0 | 0 | 90 | 30 |
| 2 | 125 | 0 | 0 | 85 | 0 |
| 1 | 125 | 0 | 0 | 60 | 0 |
| 16 | 60 | 0 | 0 | 95 | 50 |
| 8 | 60 | 0 | 0 | 90 | 30 |
| 4 | 60 | 0 | 0 | 90 | 30 |
| 2 | 60 | 0 | 0 | 85 | 0 |
| 1 | 60 | 0 | 0 | 60 | 0 |
| 16 | 30 | 0 | 0 | 90 | 50 |
| 8 | 30 | 0 | 0 | 90 | 30 |
| 4 | 30 | 0 | 0 | 85 | 30 |
| 2 | 30 | 0 | 0 | 80 | 0 |
| 1 | 30 | 0 | 0 | 30 | 0 |
| 16 | 15 | 0 | 0 | 90 | 50 |
| 8 | 15 | 0 | 0 | 80 | 30 |
| 4 | 15 | 0 | 0 | 75 | 30 |
| 2 | 15 | 0 | 0 | 70 | 0 |
| 1 | 15 | 0 | 0 | 40 | 0 |

Example B2

Field test in paddy rice:

Test plots each having a surface area of 10 m² were ploughed, flooded with water and prepared for planting with rice by puddling the surface of the soil. The plots were planted with 21-day-old rice plants of the type "Nihonbare" that were at the 2-3 leaf stage. 12 days after planting, the test plots were sprayed with a dilute aqueous dispersion of the active ingredient mixture. The plots were maintained in the flooded state. 33 days after the treatment, an evaluation was carried out in accordance with the standard given in the green-house test in comparison with the untreated control plot which had natural weed growth. The principal weed was *Scirpus juncoides*.

| Results: | |
|---|---|
| test site: | Ono, central Japan |
| type of rice: | Nihonbare |
| planting date: | 25th April 1986 |
| application: | 7th May 1986 |
| evaluation: | 9th June 1986 |
| rate of application in the form of spray liquor mixture (tank mix): | |
| compound I: | 30 g active ingredient/hectare |
| compound Vb: | 300 g active ingredient/hectare |
| compound VIII: | 250 g active ingredient/hectare |

| active ingredient | g a.i./ha | effect on "Nihonbare" rice | effect on *Scripus juncoides* |
|---|---|---|---|
| comp. I | 30 | 0 | 90 |
| comp. Vb | 300 | 0 | 20 |
| comp. VIII | 250 | 0 | 0 |

| | effect of the mixture 30 g comp. I + 300 g comp. Vb + 250 g comp. VIII | |
|---|---|---|
| | effect found | expected value |
| "Nihonbare" rice | 0 | 0 |
| *Scirpus juncoides* | 100 | 92 |

We claim:

1. A synergistic composition for selective weed control in rice, characterized in that, in addition to carriers and/or other adjuvants, it contains, in admixture with one another, as active component, on the one hand N-[2-(2-methoxyethoxy)-phenylsulphonyl]-N' (4,6-dimethoxy-1,3,5-triazin-2-yl)-urea of the formula I

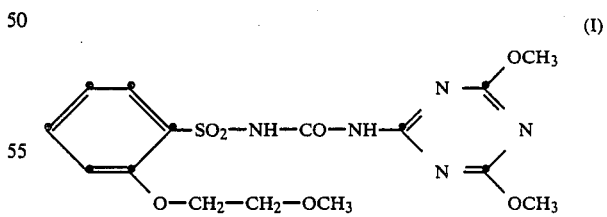

and an active ingredient of formula

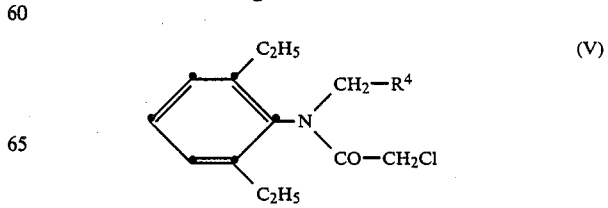

in which $R^4$ represents $C_4$–$C_4$ alkoxy or $C_1$14 $C_4$ alkoxymethyl.

2. A composition according to claim 1, characterised in that, in addition to the compound of formula I, it contains, as co-component, N-(propoxyethyl)-2-chloro-N-(2,6-diethylphenyl)-acetamide.

3. A composition according to claim 1, characterized in that, in addition to the compound of the formula I, it contains, as co-component,
N-(butoxymethyl)-2-chloro-N-(2,6-diethylphenyl-)acetamide.

4. A composition according to claim 1, characterized in that component I is present in the said composition in a ratio by weight of from 1:1 to 1:500 with respect to that of component V.

5. A method for selective weed control in rice, characterised in that the rice crop area is treated before the plants emerge with an effective amount of a composition according to claim 1.

6. A method according to claim 5, characterised in that rice crop areas in which the weeds Alisma, Ammania, Cyperus, Echinochloa, Eleocharis, Fimbristylis, Scirupus or Monochoria are expected are treated with an effective amount of a composition according to claim 1.

7. A method according to claim 5, characterised in that the rice crop is treated with the said composition at rates of application corresponding to from 0.005 to 3 kg, preferably from 0.01 to 1 kg, total amount of active ingredient per hectare.

8. A method of controlling undesirable plant growth which comprises applying an effective amount of a composition according to claim 1 for selective weed control in rice crops.

* * * * *